United States Patent
Gresham et al.

(10) Patent No.: US 8,282,604 B2
(45) Date of Patent: Oct. 9, 2012

(54) FLEXIBLE CANNULA WITH ASSOCIATED SEAL

(75) Inventors: Richard D. Gresham, Guilford, CT (US); Robert C. Smith, Middletown, CT (US)

(73) Assignee: Tyco Healthcare Group LP, Mansfield, MA (US)

( * ) Notice: Subject to any disclaimer, the term of this patent is extended or adjusted under 35 U.S.C. 154(b) by 738 days.

(21) Appl. No.: 12/122,793

(22) Filed: May 19, 2008

(65) Prior Publication Data

US 2008/0287877 A1 Nov. 20, 2008

Related U.S. Application Data

(60) Provisional application No. 60/930,745, filed on May 18, 2007.

(51) Int. Cl.
*A61M 5/178* (2006.01)
(52) U.S. Cl. .................................. 604/167.06
(58) Field of Classification Search ............. 604/164.01, 604/167.01–167.06, 174; 606/108, 185
See application file for complete search history.

(56) References Cited

U.S. PATENT DOCUMENTS

| | | | |
|---|---|---|---|
| 3,570,485 A | 3/1971 | Reilly | |
| 3,809,081 A | 5/1974 | Loveless | |
| 4,243,034 A | 1/1981 | Brandt | |
| 4,344,435 A | 8/1982 | Aubin | |
| 4,411,653 A | 10/1983 | Razi | |
| 4,451,252 A | 5/1984 | Martin | |
| 4,685,473 A * | 8/1987 | Karcher et al. | 600/585 |
| 4,934,340 A | 6/1990 | Ebling | |
| 5,058,934 A * | 10/1991 | Brannon | 285/226 |
| 5,443,448 A | 8/1995 | DeVries | |
| 5,634,911 A | 6/1997 | Hermann | |
| 5,674,240 A | 10/1997 | Bonutti et al. | |
| 5,797,888 A | 8/1998 | Yoon | |
| 5,814,073 A | 9/1998 | Bonutti | |
| 5,871,474 A | 2/1999 | Hermann | |
| 5,944,691 A | 8/1999 | Querns et al. | |
| 6,090,121 A | 7/2000 | Weber et al. | |
| 6,440,120 B1 | 8/2002 | Maahs | |
| 7,344,547 B2 | 3/2008 | Piskun | |

(Continued)

FOREIGN PATENT DOCUMENTS

EP 0630660 A 12/1994

(Continued)

OTHER PUBLICATIONS

European Search Report for EP 08251708.7-2310 date of completion is Feb. 16, 2010 (4 pages).

(Continued)

*Primary Examiner* — Christopher D Koharski

(57) ABSTRACT

A cannula assembly includes a housing and a cannula member connected to the housing. The cannula member has leading and trailing ends and defines a longitudinal axis. The cannula member further includes a main body, a seal adjacent the leading end and a flexible portion disposed between the main body and the seal. The seal is capable of receiving an instrument therethrough while maintaining a substantial sealed relation with the instrument. The flexible portion is configured to permit movement of the seal relative to the longitudinal axis during manipulation of the endoscopic instrument. The flexible portion of the cannula member may include one or more bellows. The one or more bellows may form a goose neck configuration. Alternatively, the one or more bellows define a series of ridges and grooves.

19 Claims, 7 Drawing Sheets

U.S. PATENT DOCUMENTS

| | | |
|---|---|---|
| 2003/0028179 A1 | 2/2003 | Piksun |
| 2004/0054377 A1 | 3/2004 | Foster et al. |
| 2004/0068232 A1 | 4/2004 | Hart et al. |
| 2004/0087968 A1 | 5/2004 | Core |
| 2005/0216028 A1* | 9/2005 | Hart et al. .................... 606/108 |
| 2008/0027476 A1 | 1/2008 | Piksun |

FOREIGN PATENT DOCUMENTS

| | | |
|---|---|---|
| EP | 1 454 590 A1 | 9/2004 |
| WO | WO96/23536 A | 8/1996 |
| WO | WO01/80749 A | 11/2001 |
| WO | 03/011154 A2 | 2/2003 |
| WO | WO2004066828 | 8/2004 |
| WO | WO2005/102186 A | 11/2005 |
| WO | WO2008/064344 A | 5/2008 |

OTHER PUBLICATIONS

Extended International Search Report corresponding to European Application No. EP 10 25 0720.9, completed Jul. 19, 2010; mailed Feb. 11, 2009; 6 pages.

* cited by examiner

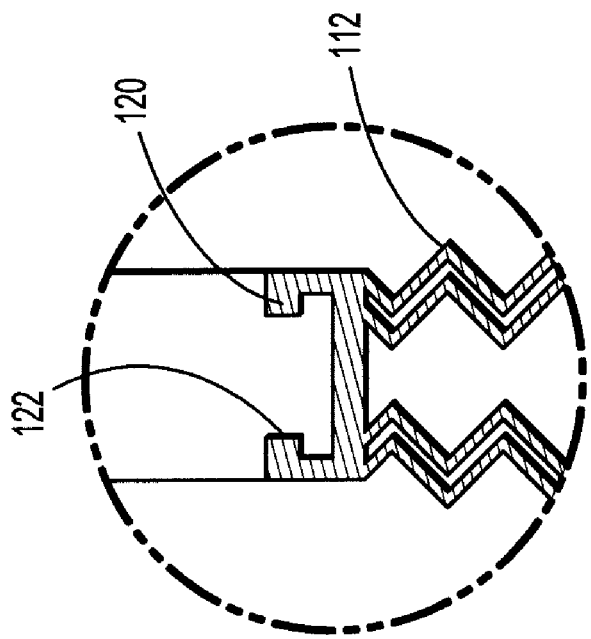
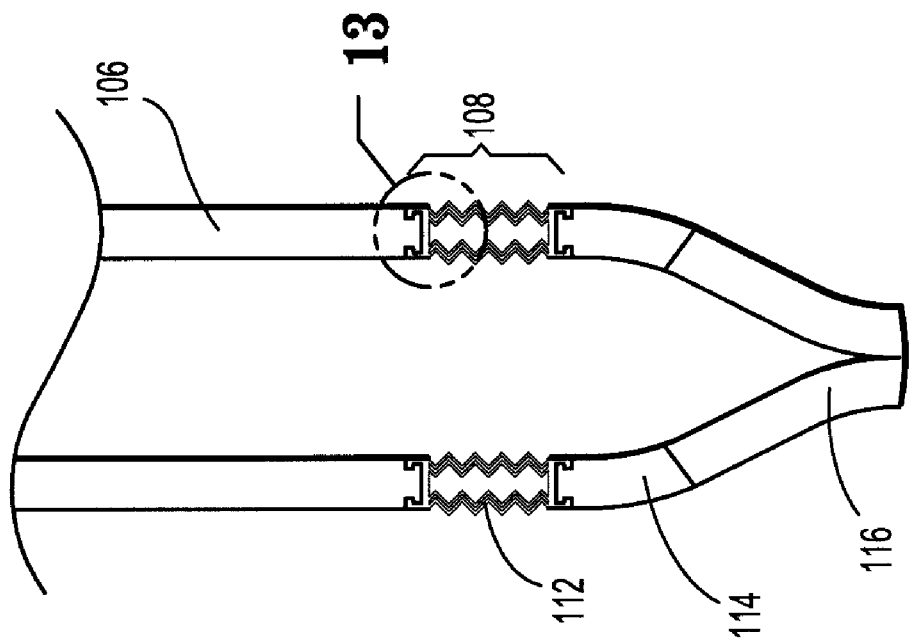

FLEXIBLE CANNULA WITH ASSOCIATED SEAL

CROSS REFERENCE TO RELATED APPLICATION

The present application claims the benefit of and priority to U.S. Provisional Application Ser. No. 60/930,745 filed on May 18, 2007, the entire contents of which are incorporated herein by reference.

BACKGROUND

1. Technical Field

The present disclosure relates generally to a system for accessing the body, and, more particularly, relates to a cannula having a seal and an associated flexible body portion adapted to permit lateral, angular or longitudinal movement of an inserted instrument while also preserving the sealed relation of the seal about the instrument during its manipulation.

2. Background of Related Art

Surgical cannulas are employed in various minimally invasive procedures including laparoscopic or endoscopic procedures. Such cannulas each typically incorporate a rigid tubular member and a seal mechanism. The seal mechanism is intended to form a fluid tight seal about an instrument or hand passed through the tubular member. The seal mechanism, however, is often limited by its ability to sustain a seal when an instrument is moved off-axis relative to a central axis of the cannula. Moreover, the seal mechanisms are also limited by their ability to sustain their integrity when the surgical instrument is angulated. Furthermore, due to the rigidity of the tubular member of the cannula, offset manipulation of the inserted instrument is restricted.

SUMMARY

Accordingly, the present disclosure is directed to a cannula assembly including a housing and a cannula member connected to the housing. The cannula member has leading and trailing ends and defining a longitudinal axis. The cannula member further includes a main body, a seal adjacent the leading end and a flexible portion disposed between the main body and the seal. The seal is capable of receiving an instrument therethrough while maintaining a substantial sealed relation with the instrument. The flexible portion is configured to permit movement of the seal relative to the longitudinal axis during manipulation of the endoscopic instrument. The flexible portion of the cannula member may include one or more bellows. The one or more bellows may form a goose neck configuration. Alternatively, the one or more bellows define a series of ridges and grooves.

The flexible portion is adapted to permit angular movement of the seal relative to the longitudinal axis. The flexible portion may be adapted to permit lateral movement of the seal relative to the longitudinal axis. The flexible portion may be adapted to permit lateral and angular movement of the seal relative to the longitudinal axis. The flexible portion may be adapted to permit longitudinal movement of the seal relative to the longitudinal axis.

The seal may be adapted to substantially close in the absence of an instrument.

In another embodiment, the cannula includes a cannula member defining a central axis and having proximal and distal ends. The cannula member includes a main body adjacent the proximal end of the cannula member, a universal seal adjacent the distal end of the cannula member and a generally flexible portion disposed between the main body and the universal seal. The universal seal may be adapted to form a substantial sealed relation about a surgical object advanced through the cannula member and is further adapted to substantially close in the absence of the surgical object. The flexible portion may be adapted to permit movement of the universal seal relative to the central axis upon manipulation of the surgical object. The flexible body portion may define at least one bellows. The flexible body portion may comprise an elastomeric material. The flexible body portion may be adapted to permit lateral movement of the universal seal relative to the central axis. The flexible body portion may be adapted to permit angular movement of the universal seal relative to the central axis. The flexible portion may be adapted to permit each of angular and lateral movement of the universal seal relative to the central axis. In the alternative, the flexible portion is adapted to permit longitudinal movement of the seal relative to the longitudinal axis.

BRIEF DESCRIPTION OF THE DRAWINGS

Preferred embodiments of the present disclosure are described hereinbelow with references to the drawings, wherein:

FIG. 12 is a side cross-sectional view of another embodiment of the present disclosure; and FIG. 13 is an enlarged cross-sectional view of the flexible portion of the trocar cannula of FIG. 12.

DETAILED DESCRIPTION

The cannula of the present disclosure is capable of accommodating objects of varying diameters, e.g., including instruments from about 4.5 millimeter (mm) to about 15 millimeter (mm), during a minimally invasive surgical procedure. Moreover, the cannula contemplates the introduction and manipulation of various types of instrumentation adapted for insertion through a trocar and/or cannula assembly while maintaining a fluid tight interface about the instrumentation to prevent gas and/or fluid leakage from the established pneumoperitoneum so as to preserve the atmospheric integrity of a surgical procedure. Specifically, the cannula includes a flexible body portion and associated distal seal which permits angular manipulation of the surgical instrument while maintaining or preserving the sealing relation formed by the seal about the instrument. This feature of the present disclosure desirably minimizes the entry and exit of gases and/or fluids to/from the body cavity and also provides enhanced capability of instrument manipulation within the operative site.

Examples of instrumentation contemplated for use with the cannula include clip appliers, graspers, dissectors, retractors, staplers, laser probes, photographic devices, endoscopes and laparoscopes, tubes, and the like. Such instruments will be collectively referred to herein as "instruments or instrumentation".

In the following discussion, the term "proximal" will refer to the portion of the access apparatus nearest to the clinician during operation while the term "distal" will refer to that portion of the access apparatus most remote to the clinician.

Figure 1:
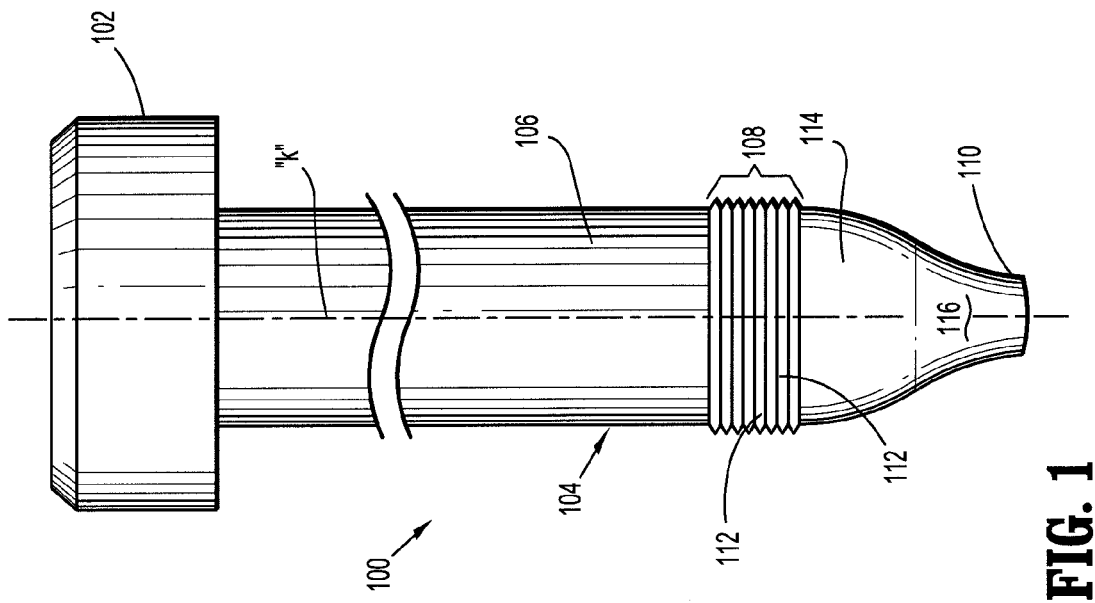
FIG. 1 is a side view of a trocar cannula according to an embodiment of the present disclosure.
Figure 3:
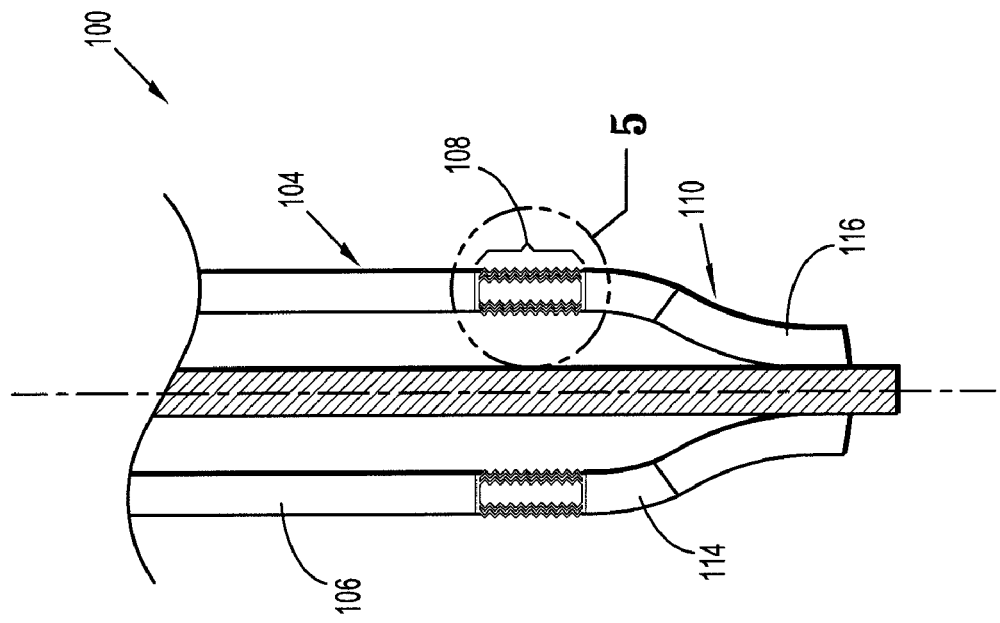
FIG. 3 is a side cross-sectional view of the distal end of the trocar cannula illustrating an instrument at least partially therein and the seal in a closed position.
Figure 4:
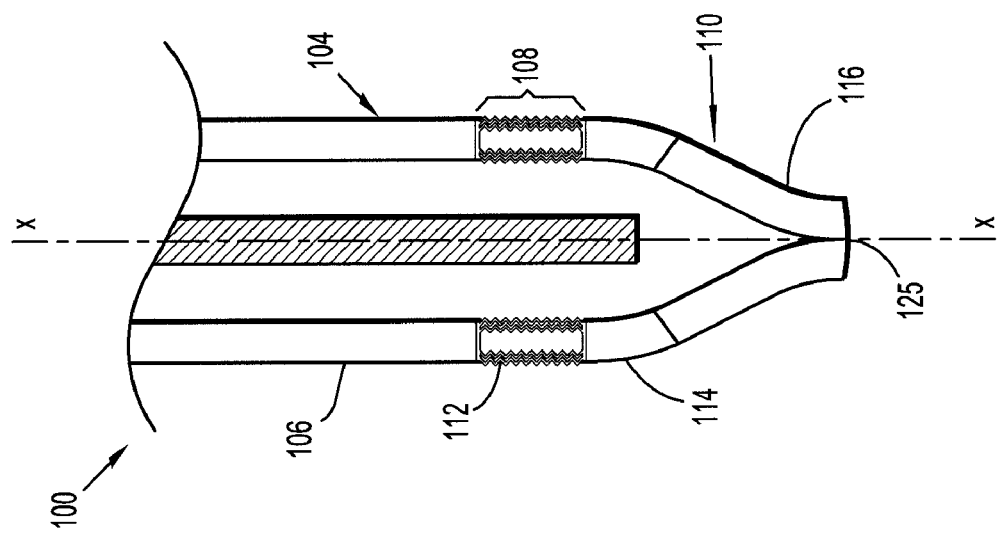
FIG. 4 is a side cross-sectional view of the distal end of the trocar cannula illustrating the instrument advanced through the seal.

Referring now to the drawings, in which like reference numerals identify identical or substantially similar parts throughout the several views, FIG. 1 illustrates the trocar cannula of the present disclosure. Cannula 100 may be any member suitable for the intended purpose of accessing a body cavity and typically defines a passageway permitting introduction of instruments or the clinician's hand therethrough. Cannula 100 is particularly adapted for use in laparoscopic surgery where the peritoneal cavity is insufflated with a suitable gas, e.g., $CO_2$, to raise the cavity wall from the internal organs therein. Cannula 100 is typically used with an obturator assembly (not shown) which may be blunt, a non-bladed, or a sharp pointed instrument positionable within the passageway of the cannula 100. The obturator assembly is utilized to penetrate the abdominal wall to introduce the cannula 100 through the abdominal wall, and then subsequently is removed from the cannula 100 to permit introduction of the surgical instrumentation utilized to perform the procedure through the passageway.

Figure 2:
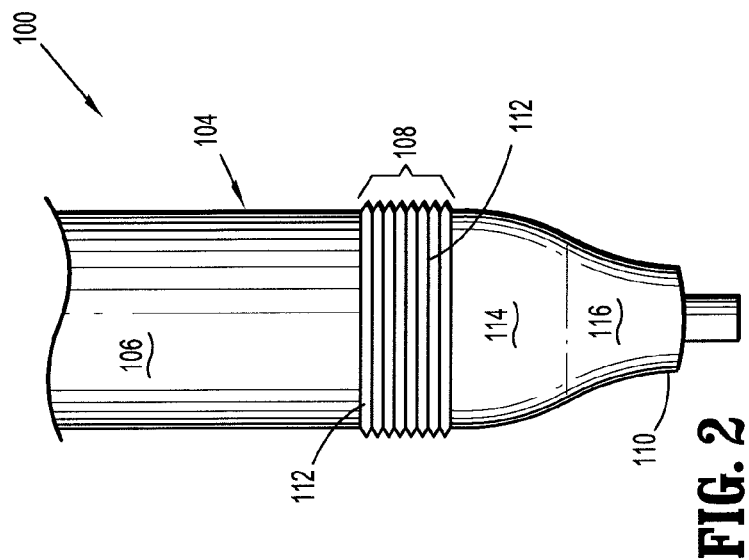
FIG. 2 is a side view of the distal end of the trocar cannula of FIG. 1 illustrating an endoscopic instrument introduced therein.

Referring initially to FIGS. 1 and 2, cannula 100 includes housing 102 and cannula member 104 extending distally from the housing 102. Either or both housing 102 and cannula member 104 may be transparent in part or in whole and may be fabricated from biocompatible metal or polymeric material. Housing 102 typically incorporates at least one internal seal which is adapted to form a fluid tight seal about an instrument inserted through the housing 102. One suitable seal may be the fabric seal disclosed in commonly assigned U.S. Pat. No. 6,702,787, which issued Mar. 9, 2004, the entire contents of which are incorporated herein by reference. The seal disclosed in the '787 patent may be a flat septum seal having a first layer of resilient material and a second fabric layer juxtaposed relative to the first layer. Further details of the seal may be ascertained by reference to the '787 patent. Housing 102 may include an internal seal such as a duck-bill valve or other zero closure valve adapted to close in the absence of a surgical instrument to prevent passage of insufflation gases through the housing 102. In one embodiment of the present disclosure, however, trocar cannula 100 is devoid of either or both an internal seal and a zero closure valve.

With reference now to FIGS. 1-4, cannula member 104 includes main body 106 adjacent housing 102, flexible portion 108 connected to the main body 106 and universal seal 110 which is distal of the flexible portion 108. Main body 106 may be substantially rigid and defines central longitudinal axis "k". Alternatively, main body 106 may have some degree of flexibility.

Figure 5:
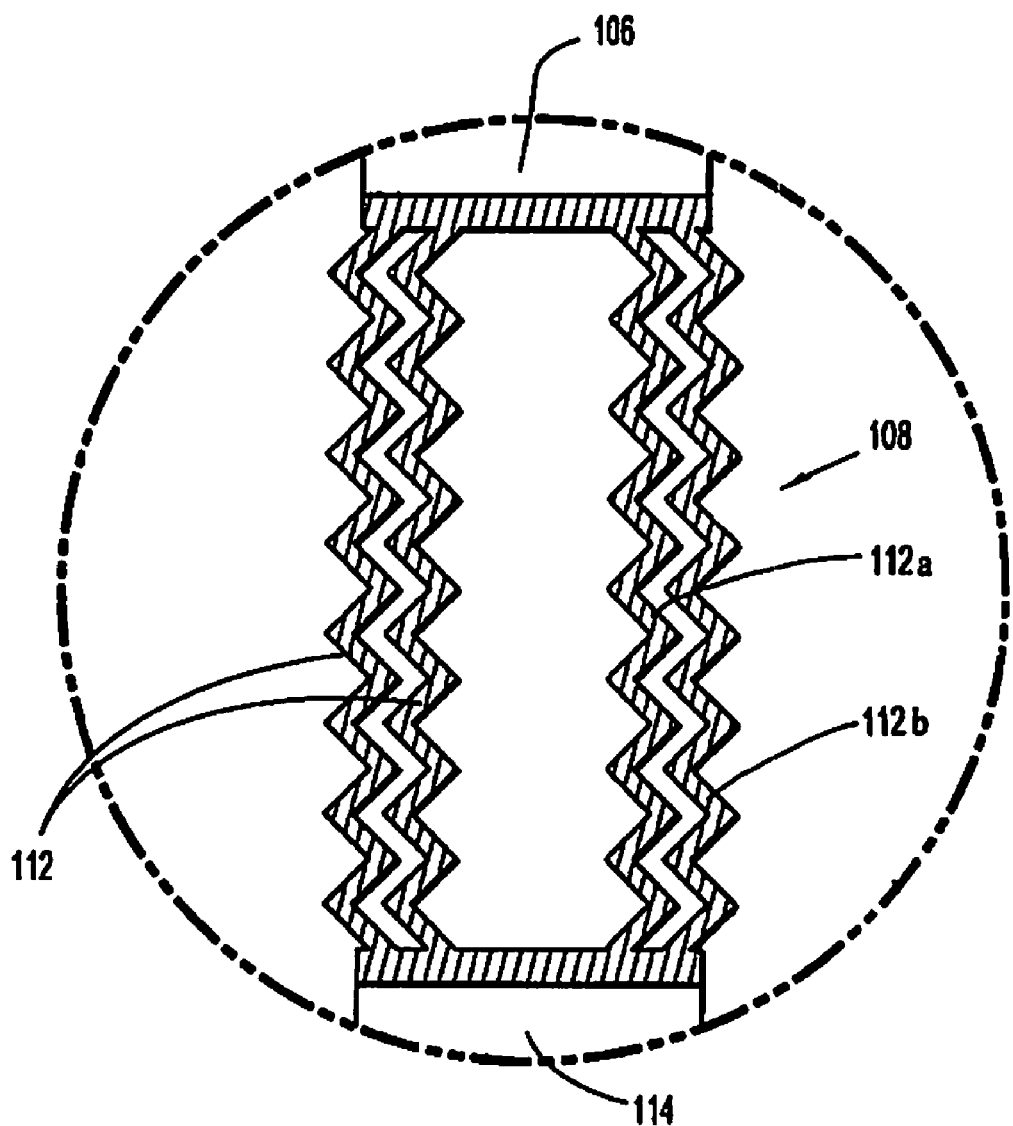
FIG. 5 is an enlarged section of the flexible portion of the trocar cannula.
Figure 6:
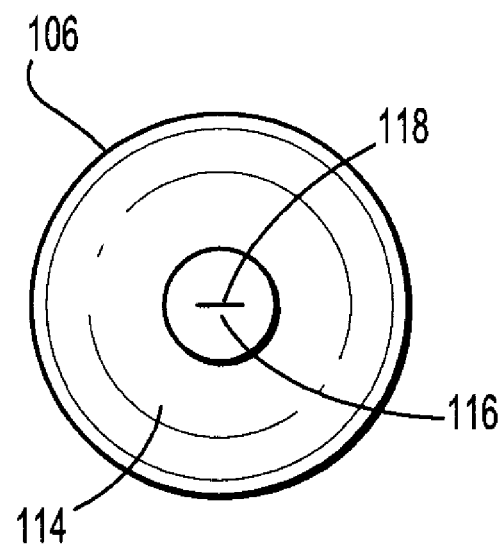
FIG. 6 is an axial view of the trocar cannula illustrating the seal in a closed position.
Figure 7:
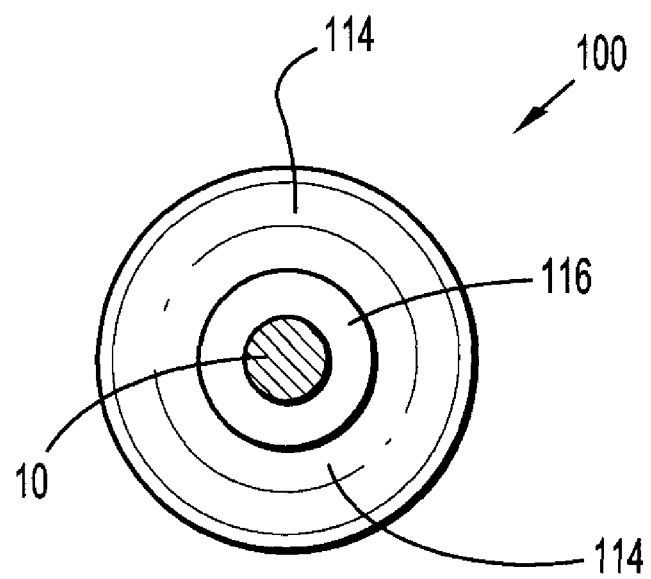
FIG. 7 is an axial view of the trocar cannula illustrating the endoscopic instrument inserted through the seal.

Flexible portion 108 is relatively flexible to permit a range of motion of universal seal 110. Such motion of universal seal 110 is inclusive of angulated motion, lateral motion and/or longitudinal motion with respect to the central longitudinal axis "k". In one embodiment, flexible portion 108 includes a bellows or goose-neck arrangement defined by at least one or a plurality or series of continuous bellows 112 or alternating convexities/ridges and concavities/recesses. For example, as seen in FIG. 5, continuous bellows 112 includes an inner bellows 112a and a generally coaxial outer bellows 112b. Continuous bellows 112 of flexible portion 108 are adapted to angulate, longitudinally extend and/or move laterally relative to each other to permit corresponding movement of universal seal 110 relative to the central longitudinal axis "k" during manipulation of the instrument.

Referring now to FIGS. 3-7, universal seal 110 will be discussed. Universal seal 110 may be adapted to close in the absence of an instrument to prevent passage of fluids, e.g., insufflation gases therethrough, e.g., to thereby assist in maintaining the integrity of the insufflated body cavity, e.g., the abdominal cavity. Universal seal 110 includes outer portion 114 and inner seal portion 116. Outer portion 114 is connected to flexible portion 112 of cannula member 104 through conventional means. Outer portion 114 may be composed of an elastomeric material, plastic, polymer, or the like. Outer portion 114 forms a tapered element depending from flexible portion 112 and is arranged to normally bias inner seal portion 116 radially inwardly to the closed position depicted in FIG. 3. Outer portion 114 also may bias inner seal portion 116 into a position in general longitudinal alignment with longitudinal axis "k". Although inner seal portion 116 is shown positioned along longitudinal axis "k", it is envisioned that the universal seal may be positioned anywhere within the diameter of cannula member 104, and may or may not be aligned with the longitudinal axis "k"

Inner seal portion. 116 is substantially flexible or resilient, and is adapted to form a substantial fluid tight seal about an instrument inserted through the inner seal portion 114. In a first or initial state, e.g., in the absence of an instrument inserted therethrough, inner seal portion 116 is closed, forming an air-tight seal as effected through the biasing action of, e.g., outer portion 114. In a second open configuration when an instrument 10 is advanced through inner seal portion 116, the inner seal portion 116 may stretch or expand to accommodate instrument 10 while maintaining an air-tight seal thereabout. Inner seal portion 116 may be configured such that an increased seal surface area is achieved upon insertion of distal end 12 of instrument 10 therethrough. This increased seal surface area permits nominal manipulation of instrument 10 without compromising the integrity of the air-tight seal. Inner seal portion 116 may be fabricated from an elastomeric material and may be integrally or monolithically formed with outer portion 114 of universal seal 110. Inner seal portion 116 may define slit 118 adapted to open to permit passage of the instrument 10. In the alternative, inner seal portion 116 may define an aperture (not shown).

Figure 8:
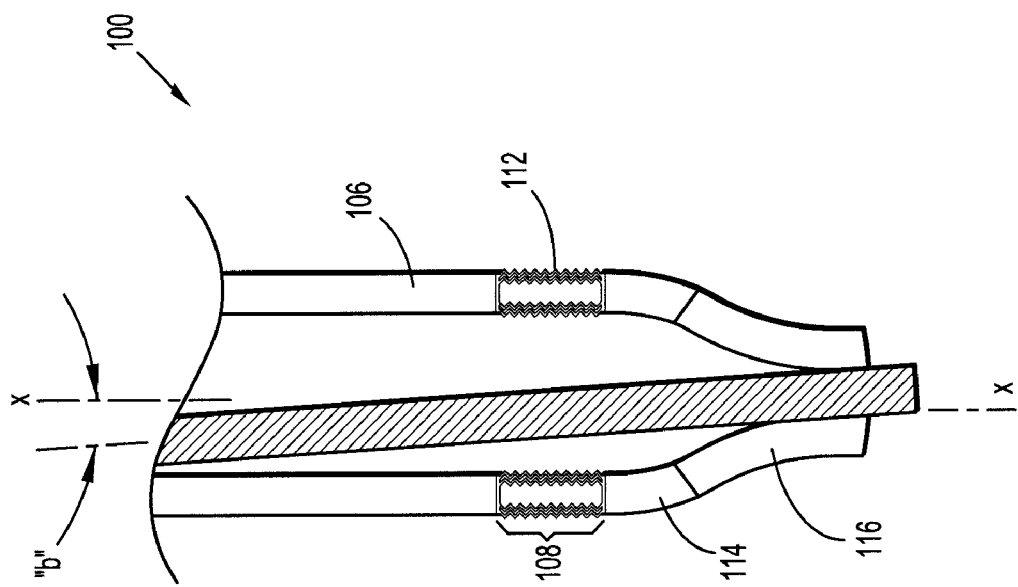
FIGS. 8-9 are side cross-sectional views of the distal end of the trocar cannula illustrating a range of offset angulated motion of the endoscopic instrument within the trocar cannula.
Figure 9:
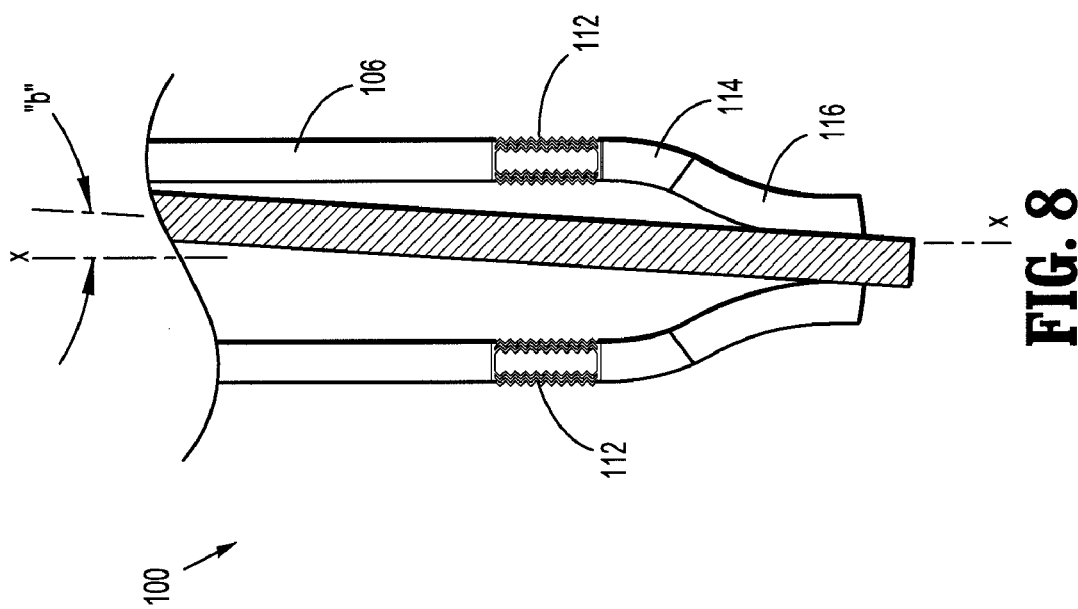

Referring to FIGS. 8 and 9, as the proximal end (not shown) of instrument 10 is handled or manipulated outside of cannula 100, any angular movement thereof may be translated to distal end 12 of the instrument. As distal end 12 is angled relative to axis "k" of cannula member 104 through a predetermined angle "b", bellows 112 of flexible portion 108 extend and/or retract accordingly to permit movement of universal seal 110 with distal end 12 of instrument 10. In this manner, the a substantial amount of seal surface area of inner seal portion 116 remains in contact about instrument 10 throughout the range of manipulation, thereby ensuring that the integrity of the seal is not compromised. As instrument 10 is angled relative to axis "k" of cannula member 104, bellows 112 of flexible portion 108 on one side, e.g., the right side extend, while the bellows 112 on the opposed side, e.g., the left side contract. (FIG. 8) The opposite is also true when instrument 10 is angled to the right relative to cannula member 104 (FIG. 9). As can been seen in FIGS. 8 and 9, the angle at which instrument 10 may be manipulated with cannula 100 is limited by the length and diameter of cannula member 104.

Figure 10:
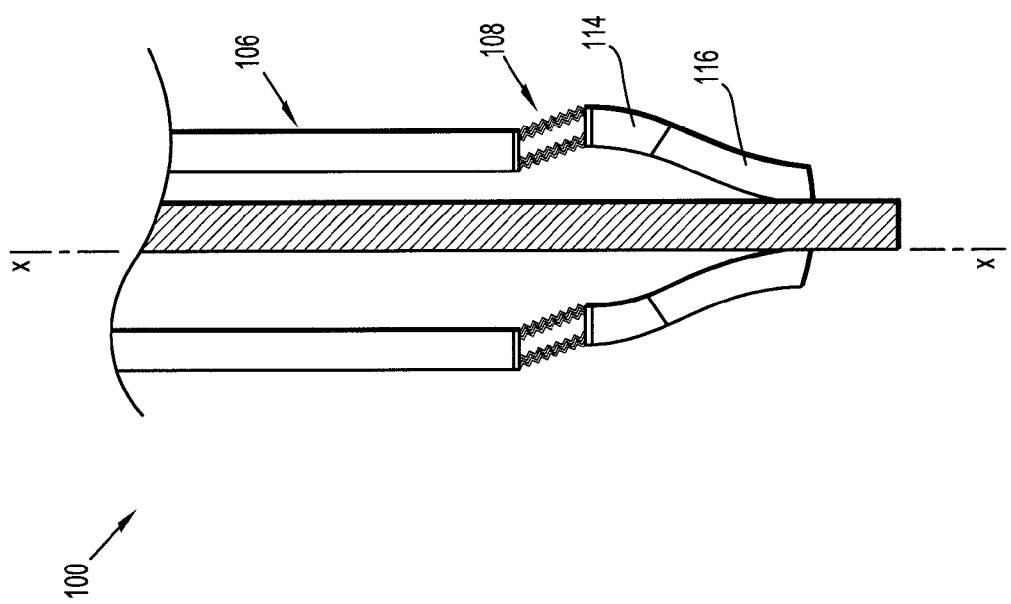
FIGS. 10-11 are side cross-sectional views of the distal end of the trocar cannula illustrating a range of offset lateral motion of the endoscopic instrument within the trocar cannula.
Figure 11:
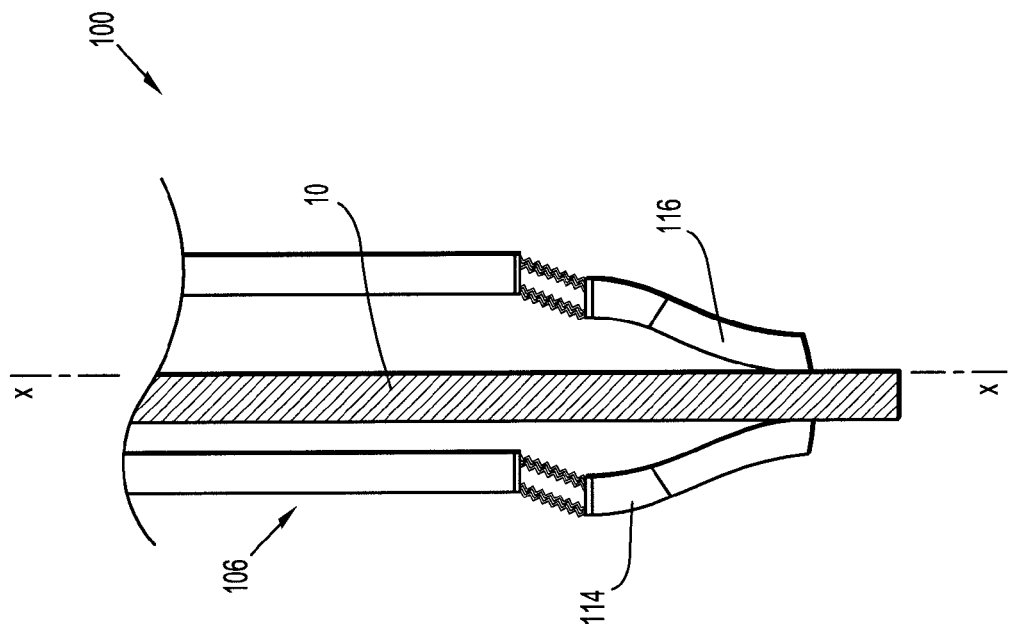

Referring now to FIGS. 10 and 11, flexible portion 108 of cannula 100 may also be configured to permit lateral manipulation of distal end 12 of instrument 10 while maintaining the integrity of the seal thereabout. As the proximal end (not shown) of instrument 10 is moved laterally within cannula 100 relative to axis "k" of cannula member 104, distal end 12 of instrument 10 may be correspondingly moved with the inner seal portion 114 of universal seal 110 also being shifted in a lateral direction. As distal end 12 of instrument 10 is shifted laterally, bellows 112 of flexible portion 108 extend or stretch to accommodate the lateral movement. In this manner, inner seal portion 116 maintains contact about instrument 10 throughout the range of manipulation, thereby ensuring that the integrity of the seal is not compromised. Both lateral and angular movement of instrument 10 and universal seal 110 is envisioned.

FIGS. 11-12 illustrate an alternate embodiment where bellows 112 of flexible portion 108 of cannula member 104 is adapted to permit longitudinal movement of the flexible portion. More specifically bellows 112 may expand and contract in accordion-like manner to increase or decrease the effective length of flexible portion 108 and cannula member 104. In this embodiment, flexible portion 108 is connected to main body 106 and universal seal 110 via a detent mechanism incorporating radially inward detents 120 of flexible portion 108 which are received within corresponding recesses 122 in main body 106 and the universal seal 110. Other means for connecting flexible portion to main body and/or universal seal are envisioned. Flexible portion 108 may also move laterally and angularly with respect to longitudinal axis "k"

Although the illustrative embodiments of the present disclosure have been described herein with reference to the accompanying drawings, it is to be understood that the disclosure is not limited to those precise embodiments, and that various other changes and modifications may be effected therein by one skilled in the art without departing from the scope or spirit of the disclosure. Other variations are also envisioned, it should be understood that various changes in form, detail and operation of the goose neck cannula of the present disclosure may be made without departing from the spirit and scope of the present disclosure.

What is claimed is:

1. A cannula assembly, which comprises:
   a housing; and
   a cannula member fluidly connected to the housing, the cannula member having leading and trailing ends and defining a longitudinal axis, the cannula member including:
      a main body;
      a seal adjacent the leading end, the seal capable of receiving an instrument therethrough while maintaining a substantial sealed relation with the instrument; and
      a flexible portion including inner and outer continuous bellows disposed between the main body and the seal, wherein each of the inner and outer continuous bellows extends completely about the longitudinal axis, the flexible portion being configured to permit movement of the seal relative to the longitudinal axis during manipulation of the endoscopic instrument.

2. The cannula assembly of claim 1 wherein the flexible portion of the cannula includes more than two bellows.

3. The cannula assembly of claim 2 wherein the bellows form a goose neck configuration.

4. The cannula assembly of claim 2 wherein the bellows define a series of ridges and grooves.

5. The cannula assembly of claim 1 wherein the flexible portion is adapted to permit angular movement of the seal relative to the longitudinal axis.

6. The cannula assembly of claim 1 wherein the flexible portion is adapted to permit lateral movement of the seal relative to the longitudinal axis.

7. The cannula assembly of claim 1 wherein the flexible portion is adapted to permit lateral and angular movement of the seal relative to the longitudinal axis.

8. The cannula assembly of claim 1 wherein the flexible portion is adapted to permit longitudinal movement of the seal relative to the longitudinal axis.

9. The cannula assembly of claim 1 wherein the seal is adapted to substantially close in the absence of an instrument.

10. A cannula comprising:
    a cannula member defining a central axis and having proximal and distal ends, the cannula member including a main body adjacent the proximal end of the cannula member, a universal seal adjacent the distal end of the cannula member and a generally flexible portion disposed between the main body and the universal seal, the universal seal adapted to form a substantial sealed relation about a surgical object advanced through the cannula member and being further adapted to substantially close in the absence of the surgical object, the flexible portion adapted to permit movement of the universal seal relative to the central axis upon manipulation of the surgical object, wherein the generally flexible portion includes coaxial inner and outer bellows being radially spaced about an entire circumference thereof.

11. The cannula of claim 10 wherein the flexible body portion defines three or more bellows.

12. The cannula of claim 10 wherein the flexible body portion comprises an elastomeric material.

13. The cannula of claim 10 wherein the flexible body portion is adapted to permit lateral movement of the universal seal relative to the central axis.

14. The cannula of claim 10 wherein the flexible body portion is adapted to permit angular movement of the universal seal relative to the central axis.

15. The cannula of claim 10 wherein the flexible portion is adapted to permit each of angular and lateral movement of the universal seal relative to the central axis.

16. The cannula of claim 10 wherein the flexible portion is adapted to permit longitudinal movement of the seal relative to the longitudinal axis.

17. The cannula assembly of claim 1 wherein the inner and outer continuous bellows are coaxial.

18. The cannula assembly of claim 1 wherein the outer continuous bellows is radially spaced from the inner continuous bellows about the entire circumference of the inner continuous bellows.

19. The cannula assembly of claim 1 wherein at least one of the main body and the seal include a detent for engaging the flexible portion.

* * * * *